Feb. 12, 1963 H. C. SWIM ETAL Plant Pat. 2,225
ROSE PLANT
Filed Feb. 26, 1962
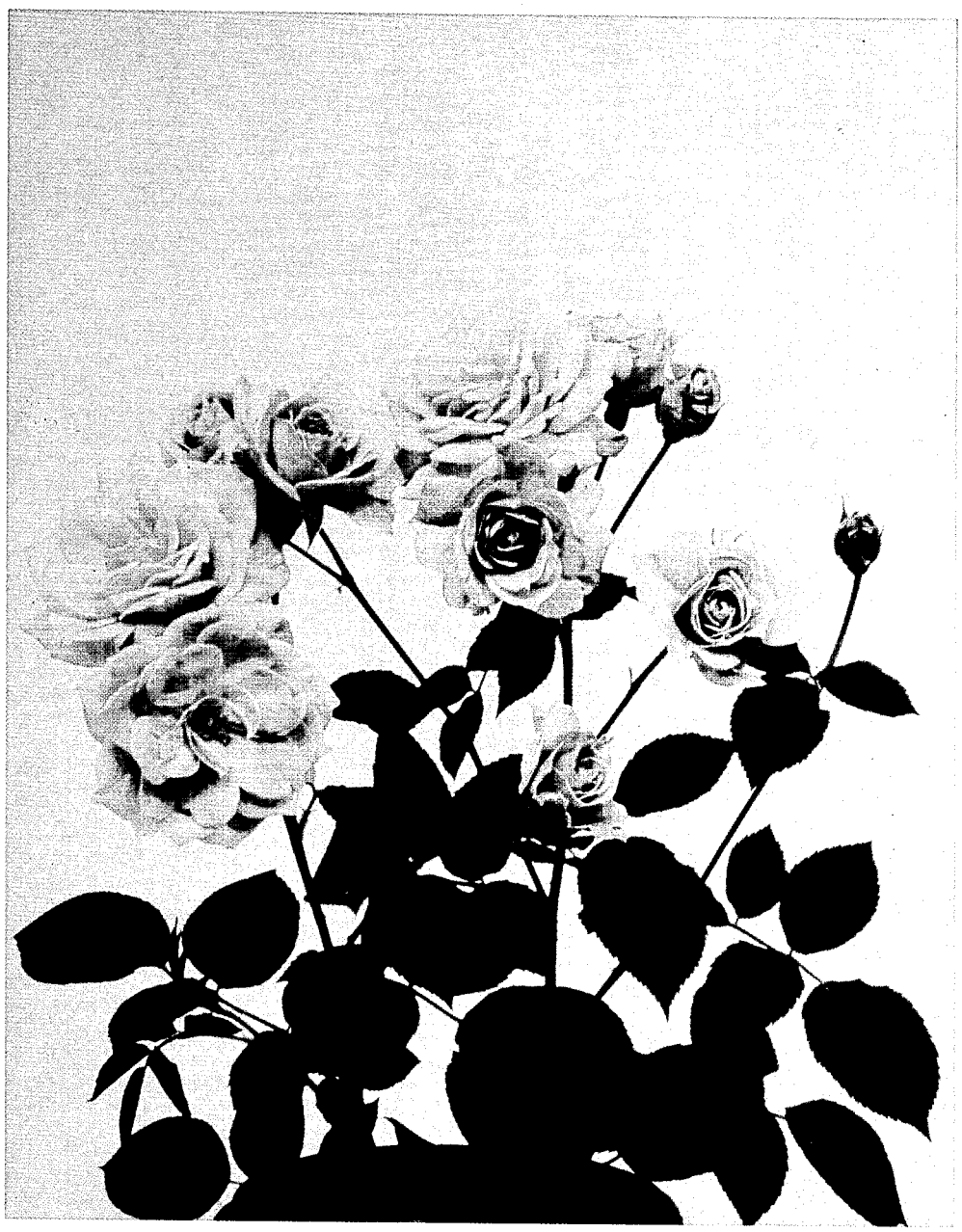
Inventors.
H. C. Swim and
O. L. Weeks
By: Robb & Robb
Attorneys United States Patent Office Plant Pat. 2,225
Patented Feb. 12, 1963

2,225
ROSE PLANT

Herbert C. Swim, Ontario, and O. L. Weeks, Chino, Calif., assignors to Armstrong Nurseries, Inc., Ontario, Calif., a corporation of California Filed Feb. 26, 1962, Ser. No. 175,860
1 Claim. (Cl. 47—61)

The present invention relates to a new and distinct variety of rose plant of the floribunda class, which was originated by us by crossing the variety "Lavender Pinocchio" (Plant Patent No. 974) with the variety "Frolic" (Plant Patent No. 1,179).

As the result of this breeding, we have produced a new rose variety which is endowed with the following unique combination of characteristics which are outstanding therein and which distinguish it from its parents, as well as from all other varieties of which we are aware:

(1) Good general health and vigor of the plant;

(2) Moderately abundant foliage of from medium to large size;

(3) Good persistence of the foliage;

(4) Good abundance of the flowers which are produced in quantity in the average sprays;

(5) An attractive and pleasing form of both the long-pointed buds and the double flowers, with the flower petals arranged regularly and being imbricated;

(6) A distinctive and attractive lilac general color tonality of the flowers; and (7) Moderate fragrance of the flowers corresponding to the fragrance of the common lilac (*Syringa vulgaris*).

In comparison with its pollen parent "Frolic," the flowers of our new variety are substantially larger, the flower petalage is greater and averages from 10 to 15 more petals per flower, the flower color ranges from lavender pink in the newly opened flower to lilac color in the older flowers, as distinguished from the pink general color tonality of the flowers of this parent, and the flower fragrance resembles the fragrance of the common lilac, as distinguished from the only slightly fragrant tea scent of the flowers of the parent variety.

As compared with its seed parent, "Lavender Pinocchio," the habit of plant growth of our new variety is more vigorous and more upright, the foliage is more persistent, the foliage is distinctly lighter green in color, the clusters of blooms in the spray average approximately twice the number of flowers in comparison with the sprays of this parent, the individual flowers average approximately ten more petals per flower than the flowers of this parent, the flowers in all stages, including the bud stage, have no brown, chocolate or olive colorations, whereas the flowers of the parent variety may be generally described as light chocolate-olive-brown in color in the bud stage, the open blooms of our new variety are lilac in general color tonality, whereas those of this parent variety are pink-lavender, and the fragrance of the flowers of our new variety distinctly resembles that of the common lilac, whereas the flower fragrance of this parent variety resembles that of a carnation.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: From half-hardy to hardy; bush; outdoor; seedling; for garden decoration.

Class: Floribunda.

Breeding: Seedling.

*Seed parent.*—"Lavender Pinocchio."

*Pollen parent.*—"Frolic."

Propagation: Holds its distinguishing characteristics through succeeding propagations by budding.

*Flower*

Locality where grown and observed: Chino, California.

Flowers borne: Occasionally singly, but usually from 2 to 10 to stem; in both irregular and regular more or less flat clusters; on long stems of normal strength.

Quantity of bloom: Abundant, both outdoors and in greenhouse.

Continuity: More or less continuous.

Fragrance: Moderate. Nature—resembles scent of common liac (*Syringa vulgaris*).

Bud:

*Peduncle.*—Short on center flower, but medium length on side blooms; medium caliper; from very slightly bending to erect; smooth, except for many small stripitate glands. Color—light green.

*Before calyx breaks.*—Size—medium. Form—long; pointed; usually without foliaceous appendages on the surface of the bud; usually without foliaceous parts extending beyond the tip of the bud. Color—near Moderate Yellow Green, Plate 7.5GY 5/7.

*As calyx breaks.*—Color—near Strong Purplish Red, Plate 7.5RP 4/11.

*As first petal opens.*—Size—medium for this type. Form—long; pointed. Color: outside—near Deep Purplish Pink, Plate 5RP 6/10 over outer areas of petal, but blending with and changing to near Brilliant Greenish Yellow, Plate 7.5Y 9/8 at base; inside—near Deep Purplish Pink, Plate 5RP 6/10 over outer portion of petal, but blending with and changing to near Brilliant Greenish Yellow, Plate 7.5Y 9/8 near base. Opening—opens up well; is retarded from opening by cold and wet weather when outer guard petals become damaged.

Bloom:

*Size (when fully open).*—Medium for type; from 2½ inches to 3 inches.

*Petalage.*—Double; stamens not hidden; from 30 to 35 or more petals, plus 5 or 6 petaloids; arranged regularly.

*Form.*—Flat at first, but becoming high-centered with age; petals being flat at first, but later becoming slightly rolled outward at maturity.

Petals:

*Texture.*—Medium thickness; medium soft. Inside—satiny. Outside—satiny.

*Shape.*—Outside—more or less truncate; often scalloped; with apex having 2 notches on extreme outer petals; others being entire and acutely pointed. Intermediate — obovate-truncate; with apex acutely pointed. Inside—narrowely obovate; with apex acutely pointed.

This description of a newly opened flower was made from a rose grown in a greenhouse during the month of January at Chino, California:

*Color.*—Outer petal: outside surface—near Moderate Purplish Pink, Plate 2.5RP 7/8, except at base where there is a small area of Light Yellow Green, Plate 7.5GY 9/4; inside surface—near Deep Purplish Pink, Plate 2.5RP 6/10, except at base which is Light Yellow Green, Plate 7.5GY 9/4, with base color sometimes extending up midrib to center of petal on extreme outer petals only. Intermediate petal: outside surface—near Moderate Purplish Pink, Plate 2.5RP 6/10, except at base which is Light Yellow Green, Plate 7.5GY 9/4; inside surface—Deep Purplish Pink, Plate 2.5RP 6/10, except at base which is Light Yellow Green, Plate 7.5GY 9/4. Inner petal: outside surface—near Moderate Purplish Pink, Plate 10P 7/7, except at base which is near Light Yellow Green, Plate 7.5GY 9/4, with latter color frequently extending entire length of midrib in a somewhat irregular broad line; inside surface—near Moderate Purplish Pink, Plate 2.5RP 6/10, except at base which is Light Yellow Green, Plate 7.5GY 9/4.

This description was made from a rose that was open for three days in a greenhouse during the month of January at Chino, California:

*Color.*—Outer petal: outside surface—Pale Purplish Pink, Plate 10P 8/5, except at base where color is near white; inside surface—Pale Purplish Pink, Plate 10P 8/5, paling toward base which is near white. Inner petal; outside surface—Pale Purplish Pink, Plate 10P 8/5, paling toward base to near white; inside surface—between Pale Purplish Pink, Plate 10P 8/5 and Moderate Purplish Pink, Plate 10P 7/7, paling toward base to near white.

*General color effect.*—Newly opened flower—near Strong Purplish Pink, Plate 5RP 7/9. Three days open—Light Purplish Pink, Plate 2.5RP 8/5.

*Behavior.*—Drop off cleanly; buds do not open properly during cold and wet weather, and are somewhat malformed.

*Flower longevity.*—Cut roses grown in greenhouse and kept at living room temperatures—6 days in January.

*Reproductive Organs*

Stamens: Medium quantity; arranged regularly in general; some tucked in calyx.

Filaments: Medium length; most with anthers. Color—yellow.

Anthers: Small; open at various times. Color—yellow.

Pollen: From moderate quantity to abundant. Color—gold.

Pistils: Medium in quantity.

Styles: Uneven; short; medium caliper; loosely bunched.

Stigma: Color—near white.

Ovaries: All enclosed in calyx.

Hips: Globular; without conspicuous neck; very smooth; walls thick and fleshy for type. Color—green.

Sepals: Permanent; moderately short; straight; spear-shaped; from curled to recurved.

Seeds: Many; small.

*Plant*

Foliage:

*Leaves.*—Compound of 3, 5 or 7 leaflets; moderately abundant; from medium to large size; moderately heavy and leathery.

*Leaflets.*—Shape—ovate; acuminate. Base—round. Margin—both singly and doubly serrate.

*Color.*—Mature: upper surface—light green, as compared with most varieties; under surface—light grey-green. Young: upper surface—bronze-red; under surface—light red.

*Rachis (the supporting stem of the compound leaf).*—Lightweight and caliper. Upper side—grooved; with few stipitate glands. Under side—sparsely prickly.

*Stipules.*—From short to medium length; moderately narrow; with short points turning out at an angle of 90°.

*Disease resistance.*—Good resistance to mildew, as compared with other varieties grown under comparable cultural conditions in the greenhouse at Chino, California.

Growth:

*Habit.*—Bushy; upright; much-branched.

*Growth.*—Vigorous.

*Canes.*—Moderately light.

*Main stems.*—Color—green, with interrupted lines of corky exudation which are numerous and more or less dominate the surface. Large prickles—many; medium length; slightly pointed downward; with medium short, medium broad base; color—brown. Small prickles—few; color—brown. Hairs—few; color—brown.

*Branches.*—Color—yellow green. Large prickles—many; medium long; from straight to slightly pointed downward; with medium long base of medium width; color—from green to brown. Small prickles—several; color—from green to brown. Hairs—few; color—from green to brown.

*New shoots.*—Color—bronze-red. Large prickles—many; medium long; straight; with short, narrow base; color—from light to green to reddish. Small prickles—several; color—reddish. Hairs—several; color—reddish.

We claim:

A new and distinct variety of rose plant of the floribunda class, substantially as herein shown and described, characterized particularly as to novelty by the unique combination of good general health and good vigor of the plant, moderately abundant foliage of from medium to large size, good persistence of the foliage, a habit of producing flowers in abundance with a good quantity of flowers in the average sprays, a pleasing and attractive form of both the long-pointed buds and the double flowers, with the flower petals being arranged regularly and being imbricated, a distinctive and attractive lilac general color tonality of the flowers, and a moderate but distinct flower fragrance corresponding to the fragrance of the common lilac (*Syringa vulgaris*).

No references cited.